United States Patent [19]

Little et al.

[11] Patent Number: 4,973,698

[45] Date of Patent: * Nov. 27, 1990

[54] PREPARATION OF 2,3-DIFLUORO-5-(TRIFLUOROMETHYL)-PYRIDINE

[75] Inventors: John C. Little, Lafayette; Charles A. Wilson, Pittsburg, both of Calif.

[73] Assignee: The Dow Chemical Company, Midland, Mich.

[*] Notice: The portion of the term of this patent subsequent to Apr. 18, 2006 has been disclaimed.

[21] Appl. No.: 300,100

[22] Filed: Jan. 23, 1989

Related U.S. Application Data

[63] Continuation of Ser. No. 125,436, Nov. 25, 1987, abandoned, which is a continuation-in-part of Ser. No. 901,714, Aug. 28, 1986, abandoned, which is a continuation-in-part of Ser. No. 665,588, Oct. 29, 1984, abandoned, which is a continuation-in-part of Ser. No. 564,800, Dec. 23, 1983, abandoned.

[51] Int. Cl.$^5$ .................. C07D 213/26; C07D 213/61; B01D 3/34
[52] U.S. Cl. ..................................... 546/345; 546/346; 203/28; 203/29
[58] Field of Search .................. 546/345, 346; 203/28, 203/29

[56] References Cited

U.S. PATENT DOCUMENTS

| | | | |
|---|---|---|---|
| 4,071,521 | 1/1978 | Muench | 546/345 |
| 4,480,102 | 10/1984 | Werner | 546/345 |
| 4,565,568 | 1/1986 | Johnston et al. | 546/345 |
| 4,745,193 | 5/1988 | Howarth et al. | 546/345 |

FOREIGN PATENT DOCUMENTS 1340421 12/1973 United Kingdom ................ 546/345

OTHER PUBLICATIONS

Finger et al., *J. Organic Chem.* 28, 166–1668 (1963).
Chambers et al., *Proc. Chem. Soc.*, 1964, p. 83.
Chambers et al., *J. Chem. Soc.*, 1964, 3573–3576.
Newkome and Paudler, *Contemporary Heterocyclic Chemistry*, pp. 262–264.
Banks et al., *J. Chem. Soc.*, 1965, 594–597.
Abramovitch, *Pyridine and its Derivatives*, Supplement Part 2, pp. 422–423.

*Primary Examiner*—Alan L. Rotman
*Attorney, Agent, or Firm*—Herlin B. Davey; D. Wendell Osborne

[57] ABSTRACT

2,3-Difluoro-5-(trifluoromethyl)pyridine is prepared by contacting a 2,3-dihalo-5-(trifluoromethyl) pyridine with an effective amount of KF or CsF in a polar aprotic solvent (diluent) at an elevated temperature under substantially anhydrous conditions with removal of the difluoropyridine products essentially as they are formed. The starting material may optionally be added as the reaction proceeds to minimize decomposition. The reaction is also optionally conducted in the presence of an acid scavenger and/or a crown ether or other phase-transfer catalyst.

9 Claims, No Drawings

PREPARATION OF 2,3-DIFLUORO-5-(TRIFLUOROMETHYL)PYRIDINE

CROSS REFERENCE TO RELATED APPLICATION

This application is a continuation of Ser. No. 125,436, filed Nov. 25, 1987, now abandoned, which is a continuation-in-part of Ser. No. 901,714, filed Aug. 28, 1986, now abandoned, which is a continuation-in-part of Ser. No. 665,588, filed Oct. 29, 1984, now abandoned, which is a continuation-in-part of Ser. No. 564,800, filed Dec. 23, 1983, now abandoned.

BACKGROUND OF THE INVENTION

The present invention relates to the preparation of 2,3-difluoro-5-(trifluoromethyl)pyridine employing potassium fluoride (KF) and/or cesium fluoride (CsF) as the fluorinating agent.

Alkali metal fluorides are well-known agents for the conversion of ring-chlorinated pyridines to the corresponding fluoropyridines. Thus, Finger, et al. (J. Org. Chem. 28, 1666 (1963)), found that KF in dimethyl sulfone at 200° C. over a period of time converted 2-chloropyridine to 2-fluoropyridine. Similarly, 2,3,5-trichloro- and 2,3,5,6-tetrachloropyridine gave the 2-fluoro- and 2,6-difluoro-3,5-dichloropyridines.

It is equally well-known that the exchange of chlorine on pyridine for fluorine using the nucleophilic action of fluoride ion very strongly favors replacement at the alpha- or gamma-positions of chloropyridines, with a beta-chlorine remaining essentially inert. Thus, in addition to the above cases, it has been noted by Chambers, et al. (Proc. Chem. Soc. 1964, 83) that pentachloropyridine, for example, strongly favors exchange at the alpha- and gamma-positions when heated to ca. 200° C. in a polar, aprotic diluent, and only under extreme conditions (anhydrous KF, 400°–500° C., 24 hr) does the exchange of the beta (3- and 5-) chlorines occur. Moreover, whenever this exchange at the beta (3- and/or 5-) position has been observed, it has been limited to fully-substituted chloropyridines: the above-mentioned 2,3,5,6-tetrachloropyridine (having a hydrogen at the 4-position) gives only decomposition products under these conditions (Chambers, loc cit.). In closely-related substitution reactions, a beta-chloropyridine has been found to be 10,000–100,000 times less reactive than the alpha-chloro- or gamma-chloropyridine, and theoretical explanations have been offered (Newkome and Paudler, "Contemporary Heterocyclic Chemistry", New York, John Wiley (1982), pp 262-3).

Scovell et al, in European patent application No. 63,872 confirm the relative inactivity in substitution reactions of chlorine in the beta position of the pyridine nucleus. They teach the reaction of chloropyridines with KF, in the presence or absence of a polar aprotic diluent, in order to replace chlorine by fluorine except that when 2,3-dichloro-5-(trichloromethyl)pyridine is allowed to react with KF the chlorine in the 3-position (beta-position) remains unchanged while all the other chlorine atoms are replaced by fluorine. The resulting product is 3-chloro-2-fluoro-5-(trifluoromethyl)pyridine (I). Thus Scovell et al support the findings of Newkome and Paudler to the effect that beta-chloropyridines have been found to be 10,000–100,000 times less reactive than alpha- or gamma-chloropyridines.

Similarly, the use of CsF as a fluorinating agent is taught in, e.g., European patent applications 104,715 and 97,460. These applications teach what are believed to be the first examples of direct substitution (with fluoride ion) of fluoride for the chlorine on a 3-chloropyridine having hydrogen on the ring. EP 97,460 cites the reaction of CsF with 3-chloro-2-cyano-5-(trifluoromethyl)pyridine, II, to yield the beta-fluoropyridine, III.

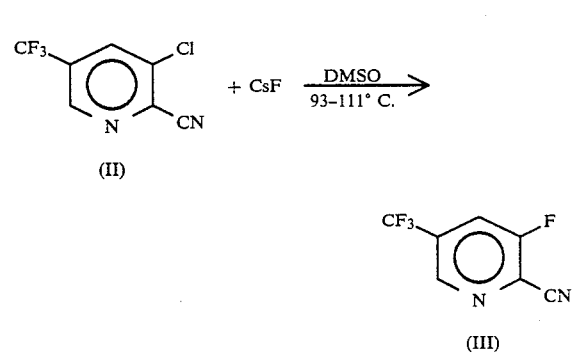

In this example, the well-known influence of an adjacent cyano group on an aromatic ring, which powerfully activates a halogen (chlorine) towards substitution (by fluoride), is believed to be operating.

EP 104,715 discloses that fluoride ion from cesium fluoride in an aprotic diluent will react with 3-chloro-2-fluoro-5-(trifluoromethyl)pyridine (I) to give 2,3-difluoro-5-(trifluoromethyl)pyridine, IV:

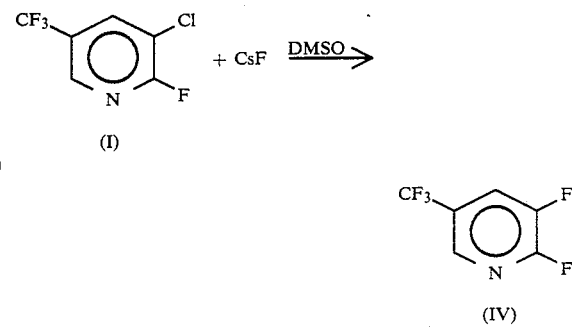

This reference teaches in a preferred embodiment the use of about 50% molar excess of CsF in dimethyl sulfoxide (DMSO) diluent at 120°–125° for about 48 hours, and the method gives yields of 48–58% IV.

SUMMARY OF THE INVENTION

We have now found that, contrary to the express teachings of Scovell et al and Newkome and Paudler, 2,3-difluoro-5-(trifluoromethyl)pyridine can be prepared in high yields by a process which comprises contacting, under reactive conditions in a liquid medium, a reactant compound having the formula

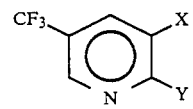

wherein X is Cl or Br and Y is Cl, Br, F or I with an effective amount of KF, by removing the product essentially as it is formed. Optionally the reactant compound may be added as the product is removed.

Applicants have made the discovery that by removing the product as it is being formed, a solution to the problem set out in Scovell et al and Newkome and Paudler, supra, is obtained, and 2,3-difluoro-5-(trifluoromethyl)pyridine is prepared and recovered in high yields.

The present invention represents a substantial improvement over the process taught in the above EP application No. 104,715, in that yields are much improved, reaction times are shorter, and the reaction may be effectively carried out with both CsF and the much less expensive KF.

DETAILED DESCRIPTION OF THE INVENTION

Of particular interest in the practice of the present invention is a method of preparing 2,3-difluoro-5-(trifluoromethyl)pyridine (II) from 3-chloro-2-fluoro-5-(trifluoromethyl)pyridine (I):

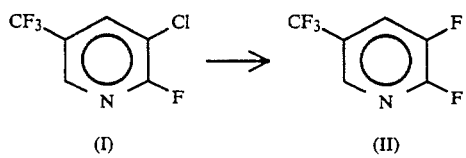

Compound II is useful as a chemical intermediate in the preparation of 2-(4-((3-fluoro-5-(trifluoromethyl)-pyridinyl)-2-oxy)phenoxy propionic acid and agriculturally acceptable derivatives thereof, i.e., salts, esters and amides, which are known herbicidal agents as described in EP No.97,460.

In a variant of this invention, Compound I may optionally be generated in situ by starting with Compound III and taking advantage of the previously-mentioned, well-known tendency of alpha-halopyridines to exchange with fluoride ion. Under the reaction conditions, use of additional fluoride (KF or CsF) allows the generation of the required alpha-fluoro-beta-halopyridine, which is then converted to the desired product.

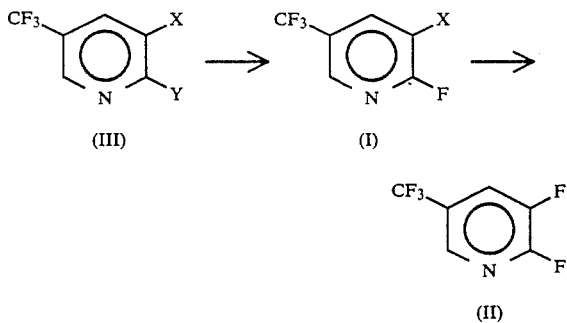

KF and CsF are the fluorinating agents employed in the present reaction and are commercially available compounds. Substantially anhydrous and finely-divided KF or CsF are preferred. Amorphous or spray-dried forms are particularly preferred. Substantially anhydrous KF and CsF can be prepared, for example, by drying in vacuo at 140°-250° C. for several hours.

Polar aprotic diluents are employed as the reaction medium in the present process. Suitable polar aprotic diluents include dimethylsulfoxide (DMSO), dimethylformamide (DMF), dimethylacetamide, diethylacetamide, methyl isobutyl ketone, hexamethylphosphoric acid triamide, tetramethylunea, sulfolane (tetramethylenesulfone), and N-methylpyrrolidinone (NMP). Preferred diluents include NMP, DMSO and sulfolane.

Optionally, the reaction may be conducted in the presence of (a) an acid scavenger, such as, an alkali metal carbonate, and/or in the case of employing KF as the fluorinating agent, (b) a phase-transfer catalyst.

The present reaction is conducted under substantially anhydrous conditions at elevated temperatures of from about 50° C. up to the boiling point of the solvent. Preferred temperature ranges are from about 100° C. to 200° C. when CsF is used, and from 150° C. up to the boiling point of the solvent when KF is used.

Pressures of from about 10 mmHg to 10 atm may also be employed, with preferred pressures of about 50 mmHg to 1 atm.

A fractional distillation system having 1 to 100 theoretical plates is conveniently employed to separate the product from the starting material. A preferred system has 5 to 20 theoretical plates.

The optimum combination of temperature and pressure is actually a function of the particular system being studied and can be determined by routine experimentation. In general the pressure is chosen so as to provide convenient separation of the desired product from the starting material through the fractional distillation system while allowing a reaction temperature (distillation pot temperature) high enough to maintain a satisfactory reaction rate. Experimental determination of the reaction rate can be conveniently judged by observing the drop in the observed reflux temperature in the distillation column from that of the starting material to that of the product.

When 2,3-difluoro-5-(trifluoromethyl)pyridine (IV) is being prepared from 3-chloro-2-fluoro-5-(trifluoromethyl)pyridine (I) using KF and NMP, for example, a pressure of 1 atmosphere and reaction temperatures of 190°-205° C. are optimally employed. When CsF and DMSO are used to effect the same conversion, a pressure of 150 mm and reactor temperatures of 120°-140° C. are conveniently used.

Substantially anhydrous reaction conditions are preferred; these may be achieved employing standard drying techniques. For example a typical glass laboratory reactor can be dried by distilling the polar aprotic solvent under a vacuum before addition of the reactants. Optionally, a small amount (5-10 percent by weight of the polar aprotic solvent) of a non-polar solvent such as an aromatic hydrocarbon (toluene, xylene, etc.) may be added to the polar aprotic solvent to aid in the removal of water by azeotropic distillation. Residual water in the reactor system is also often removed by azeotropic distillation.

The amount of polar aprotic solvent is not critical but it is advantageous to employ enough solvent to keep the starting material in solution at reaction temperatures, generally about 2 to about 25 parts by weight solvent per part by weight pyridine starting material. The relative proportions of reactants to be employed are not critical because some of the product will be formed when employing any proportion of reactants. The reaction consumes the reactants, however, in the ratio of one mole of fluorinating agent per mole of exchangeable halogen atoms present in the starting material. For example, if 2,3-dichloro-5-(trifluoromethyl)pyridine is the starting material, then about 2 molar equivalents of KF or CsF per molar equivalent pyridine starting material can be employed, and if 3-chloro-2-fluoro-5-(trifluoromethyl)pyridine is the starting material, then about equimolar amounts of KF or CsF and pyridine starting material can be employed. Usually from about 0.75 to about 1.5 moles of KF or CsF are employed per mole of exchangeable halogen in the pyridine starting material.

In carrying out the present reaction, neither the rate nor the order of addition of the reactants is critical. Usually, the solvent and fluorinating agent are added to an appropriate reaction vessel and the reaction is dried by distilling a small portion of the solvent. The starting material or precursor compound is then added to the reaction vessel which is thereafter followed by heating of the reaction mixture at a suitable pressure, usually 50 mmHg to 1 atm, to provide convenient separation of the desired product as it is formed. In an especially preferred mode, the starting material is added to the fluorinating agent (KF or CsF) in the solvent under the optimized reaction conditions at about the same molar rate as the formation and removal of the product. If an acid scavenger, a non-polar solvent, or catalyst is employed in the reaction, then they are advantageously added to the solvent/fluorinating agent mixture prior to drying the reactor vessel.

The present reaction is typically conducted in the presence of agitation sufficient to maintain an essentially uniform dispersion of the reactants in the solvent.

Usually the reaction using KF without a catalyst is complete in 16 to 24 hours. Catalysts are optionally employed, when KF is used, to increase the reaction rate. When a catalyst is used with KF, 8 to 16 hours are usually required. When CsF is used, 2 to 8 hours are normally sufficient. Suitable catalysts include phase-transfer catalysts. The catalyst is added to the present reaction mixture in an amount of from about 0.0001 to about 0.1 mole per mole of pyridine starting material, advantageously from about 0.001 to about 0.075 molar equivalents and preferably from about 0.01 to about 0.05 molar equivalents.

Phase-transfer catalysts are well known compounds and include (a) quaternary ammonium or phosphonium salts containing 10 or more carbon atoms and (b) macrocyclic polyethers commonly known as crown ethers. Suitable crown ether catalysts include 18-crown-6; dicyclchexano-18-crown-6; dibenzo-18-crown-6; 15-crown-5. A related species, tris(3,6-dioxaheptyl)-amine is also efficaceous. Suitable quaternary ammonium and phosphorium salts include tetra-n-alkylammonium salts and tetra-n-alkylphosphonium salts. Particular catalysts include benzyltriethylammonium chloride, methyl trioctylammonium chloride, tetra-n-butylammonium chloride, tetra-n-butylammonium hydrogen sulfate, tetra-n-butylphosphonium chloride and cetyl trimethylammonium bromide. The anion of the phosphonium and ammonium salts of $F^{\ominus}$ or any anion which readily converts to $F^{\ominus}$, such as for example, $Cl^{\ominus}$, $Br^{\ominus}$, $I^{\ominus}$, $OH^{\ominus}$, $OAc^{\ominus}$, etc. Preferred catalysts include 18-crown-6 and cetyltrimethylammonium bromide.

Acid scavengers are optionally employed in the present reaction to consume or inactivate traces of HCl or HF which may be present or generated during the reaction. Suitable acid scavengers include alkali metal carbonates such as anhydrous $K_2CO_3$ and anhydrous $NaCO_3$. A preferred acid scavenger is anhydrous $K_2CO_3$. The acid scavengers are added to the present reaction mixture in an amount of from about 0.001 to about 0.1 mole per mole of pyridine starting material. Preferably, from about 0.03 to about 0.05 molar equivalents are employed.

The solvent used in the process of this invention may be distilled to recover it free from impurities and re-used. Alternatively, it has been found that, under certain conditions, the solvent may be re-used without distillation by simply filtering or decanting from the spent potassium or cesium salts and charging fresh KF or CsF. Solvents such as NMP have been re-used as many as 4 times in this manner before further purification was necessary, and additional recycles may be possible.

The following examples illustrate the practice of the present invention and should not be construed as limiting. No attempt has been made to balance any chemical equations described herein. All temperatures are in °C. and boiling points are at atmospheric pressure unless otherwise stated.

EXAMPLE 1

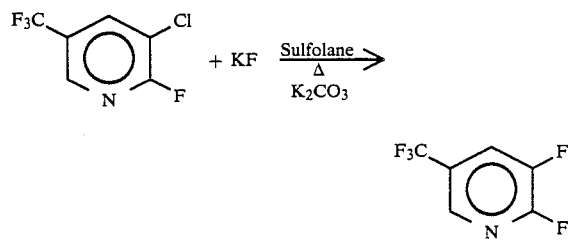

A one-liter 3-necked flask was equipped with an efficient stirrer, a thermometer, temperature controller, 250 watt infrared heat lamp, a reduced pressure control device and a 1″ OD 7-tray glass Oldershaw (sieve plate) distillation column having a vapor fraction cutter, condenser and a water-jacketed receiver. This flask was charged with 500 milliliters (ml) of sulfolane (tetramethylene sulfone), 43.5 grams (g) (0.75 mole) of KF which had been dried in vacuo at 140° C. for 48 hours and then pulverized, and 5 g of anhydrous potassium carbonate.

This mixture was heated with vigorous stirring under 100 millimeters (mm) pressure and 10-15 ml of sulfolane was distilled (head temperature raised to 209° C./100 mm) to dry the system. The vacuum was released and 100 g (0.5 mole) of 3-chloro-2-fluoro-5-(trifluoromethyl)pyridine was added to the reaction mixture. The reaction mixture was stirred at atmospheric pressure for 16 hours, the pot temperature was reduced, and a vacuum of 100 mm was applied to the system to begin distillation with continued stirring. A total of 32 g of colorless oil, having a boiling point (b.p.) of 54°–75° C./100 mm, was removed over 1½ hours, with the pot temperature being 144° C. Gas-liquid phase chromatographic (glpc) analysis indicated the presence of 27 g of desired product and 4 g of starting material.

The reaction mixture was then heated again to 220° C./1 atm with continued good stirring for 4½ hours. The pot was cooled and the pressure again reduced to 100 mm to resume distillation. A total of 23.6 g of colorless oil having b.p. 54°–67° C./100 mm, was removed while raising the pot temperature to 203° C.; glpc analysis showed an additional 21.8 g of desired product and 1.5 g of starting material. Continued heating of the reaction mixture for 15 hours at 220° C./1 atm followed by a third distillation yielded only an additional 3.1 g of oil found by glpc analysis to be 69% desired product and 13% starting material. Total yield of 2,3-difluoro-5-(trifluoromethyl)pyridine was 60% at 94% conversion of starting material.

Redistillation of the combined fractions gave substantially pure 2.3-difluoro-5-(trifluoromethyl)pyridine as a colorless oil having a b.p. of 104°-106° C. The proton and fluorine nuclear magnetic resonance (NMR) spectra were consistent with the assigned structure.

EXAMPLE 2

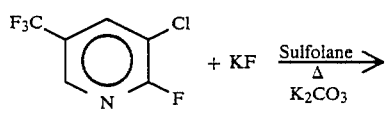

To the same apparatus as described in Example 1, was charged 550 ml of sulfolane, 43.5 g (0.75 mole) of KF (dried in vacuo 48 hours at 140°-160° C. and then pulverized) and 5 g of $K_2CO_3$. About 10 ml of sulfolane and water was distilled (b.p. 53°-210° C./100 mm) to dry the system and then the vacuum was released to add 100 g (0.5 mole) of 3-chloro-2-fluoro-5-(trifluoromethyl)pyridine. Heating was resumed at 201°-202° C. with vigorous stirring, and the distillation head temperature was observed to drop from 139° C. to about 117° C./1 atm over 2 hours, at which point slow distillation (20-40:1 reflux) was begun. Over the next 25 hours, 36 g of liquid, b.p. 109°-122° C./1 atm, containing (by glpc) 30.9 g of desired product and 5.4 g of starting material, was obtained, while the pot temperature was slowly increased to 225° C. The pot was then cooled and the pressure reduced to 250 mm at this point, and an additional 20.6 g of material, containing 18.7 g of desired product and 0.3 g of starting material, was recovered, b.p. 53°-90° C./250 mm. The yield of 2,3-difluoro-5-(trifluoromethyl)pyridine was 60% at 94% conversion of starting material. Redistillation of this product at atmospheric pressure gave excellent recovery of both desired product and starting material.

EXAMPLE 3

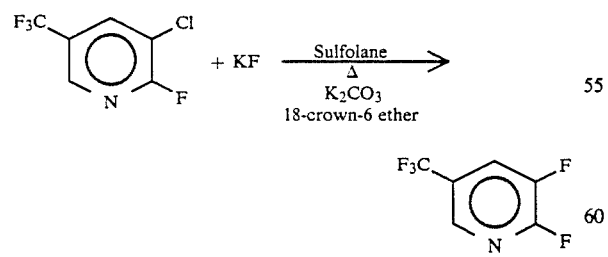

To the same apparatus as described in Example 1 was charged 515 ml of sulfolane, 43.5 g (0.75 mole) of KF which had been dried at 140° C. in vacuo for 48 hours and then pulverized, 5 g of $K_2CO_3$ and 5 g of 18-crown-6 ether. The system was dried by distillation of about 25 ml of solvent (b.p. 160°-121° C./100 mm) and then 100 g (0.5 mole) of 2,3-difluoro-5-(trifluoromethyl)pyridine was added after releasing the vacuum on the system. The mixture was stirred vigorously at 195°-200° C./1 atm for 1 hour during which time the observed head temperature dropped rapidly to about 114° C., and then distillation was begun. A total of 45.4 g of distillate was taken off over 5 hours at 111°-118° C./1 atm, and glpc analysis indicated the presence of 40.9 g of desired product.

The reaction mixture was then allowed to stir an additional 15 hours at 220° C./1 atm. Distillation yielded an additional 24.4 g of material having a b.p. of 53°-180° C./100 mm and containing 22.9 g of desired product and 0.4 g of starting material as indicated by glpc analysis. The total yield of 2,3-difluoro-5-(trifluoromethyl)pyridine was 71% at 98% conversion of starting material.

EXAMPLE 4

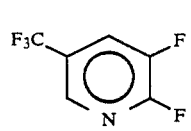 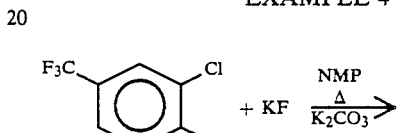

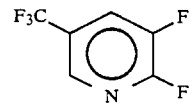

To a 2 l flask, equipped as described in Example 1, was charged one liter (1 l) of N-methyl pyrrolidinone (NMP) which was heated under 20 mm at 120° C. to dry the system. About 20 ml of NMP and water were removed. The vacuum was released and 100 g (1.7 moles) of KF (dried in vacuo 24 hours at 140°-160° C. and then pulverized), 20 g of $K_2CO_3$ (anhydrous) and 400 g (2.0 moles) of 3-chloro-2-fluoro-5-(trifluoromethyl)pyridine were added. Heating was resumed with vigorous stirring under a nitrogen atmosphere fed into the top of the reaction flask. The temperature was increased to 190°-195° C. and the distillation head temperature was observed to drop from 138° C. to 104° C. over 2 hours, at which point slow product takeoff (120/1 reflux to takeoff) was begun. Over the next 21 hours 211 g of distillate were recovered. The distillate contained 10% starting material and 90% 2,3-difluoro-5-(trifluoromethyl)pyridine equivalent to 190.2 g (61% yield) based on KF as indicated by glpc.

EXAMPLE 5

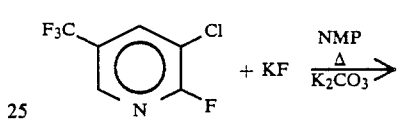 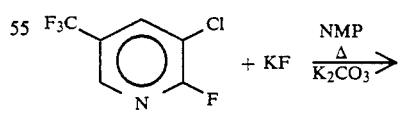

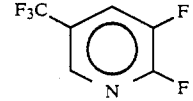

To 3 l flask, equipped as described in Example 1, was charged 1.3 l of N-methyl pyrrolidinone (NMP) which was heated under 20 mmHg at 120° C. to dry the system. About 20 ml of NMP and water were removed.

The vacuum was released and 116 g (2 moles) of KF (dried in vacuo 24 hours and then pulverized), 20 g of K$_2$CO$_3$ (anhydrous) and 500 g (2.5 moles) of 3-chloro-2-fluoro-5-(trifluoromethyl)pyridine were added. Heating was resumed with vigorous stirring under a nitrogen atmosphere fed into the top of the reaction flask. The temperature was increased to 190°–195° C. and the distillation head temperature was observed to drop from 138° C. to 104° C. over 2 hours, at which point slow product takeoff (120/1 reflux to takeoff) was begun. Over the next 16 hours, 389 g of distillate were recovered. The distillate contained 24.5% starting material and 75.5% 2,3-difluoro-5-(trifluoromethyl)pyridine equivalent to 294 g (80% yield) based on KF as indicated by glpc.

EXAMPLE 6

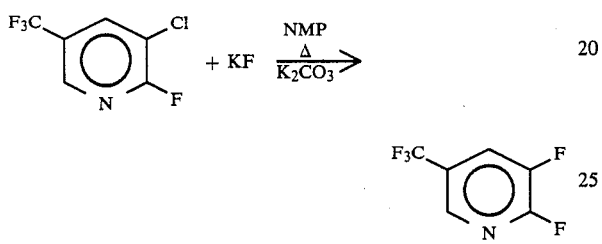

To a 3 l flask, equipped as described in Example 1, was charged 2 l of N-methyl pyrrolidinone (NMP) which was heated under 20 mm at 120° C. to dry the system. About 20 ml of NMP and water were removed. The vacuum was released and 116 g (2 moles) of KF (dried in vacuo 24 hours at 140°–160° C. and then pulverized), 10 g of K$_2$CO$_3$ (anhydrous) and 400 g (2.0 moles) of 3-chloro-2-fluoro-5-trifluoromethylpyridine were added to the flask. Heating was resumed with vigorous stirring under a nitrogen atmosphere fed into the top of the reaction flask. The temperature was increased to 190°–195° C. and the distillation head temperature was observed to drop from 138° C. to 104° C. over 2 hours, at which point a slow product takeoff (120/1 reflux to takeoff) was begun. Over the next 20 hours 283 g of distillate were recovered. The distillate contained 12% starting material and 88% 2,3-difluoro-5-(trifluoromethyl)pyridine equivalent to 249 g (68% yield) based on KF.

EXAMPLE 7

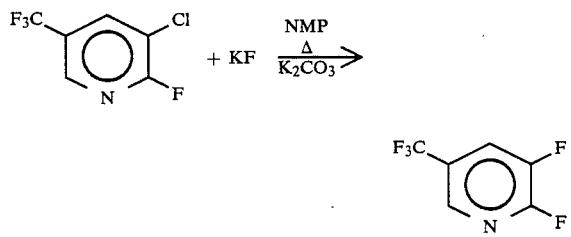

To a 3 l flask, equipped as described in Example 1, was charged 2 l of N-methyl pyrrolidinone (NMP) which was heated under 20 mm at 120° C. to dry the system. About 200 ml of NMP and water were removed. The vacuum was released and 174 g (3 moles) of KF (dried in vacuo 24 hours at 140°–160° C. and then pulverized), 20 g of K$_2$CO$_3$ (anhydrous) and 800 g (4 moles) of 3-chloro-2-fluoro-5-trifluoromethylpyridine were added slowly to the flask over a 6 hour period. Heating was resumed with vigorous stirring under a nitrogen atmosphere fed into the top of the reaction flask. The temperature was increased to 190°–195° C. and the distillation head temperature was observed to drop from 138° C. to 104° C. over ½ hour, at which point a slow product takeoff (40/1 reflux to takeoff) was begun. Over the next 22 hours 532 g of distillate were recovered. The distillate contained 15% starting material and 85% 2,3-difluoro-5-(trifluoromethyl)pyridine equivalent to 452 g (82% yield) based on KF.

EXAMPLE 8

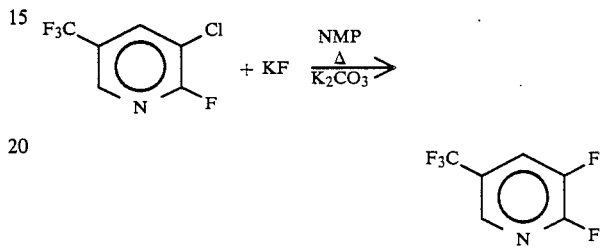

To a 3 l flask, equipped as described in Example 1, was charged 2 l of N-methyl pyrrolidinone (NMP) which was recovered from Example 8 by removing the KCl salt formed in the reaction by filtration and returning the solvent to the reaction flask. 174 Grams (3 moles) of KF (dried in vacuo 24 hours at 140°–160° C. and then pulverized), 20 g of K$_2$CO$_3$ (anhydrous) and 800 g (4 moles) of 3-chloro-2-fluoro-5-(trifluoromethyl)pyridine were added slowly to the flask over an 8 hour period. Heating was resumed with vigorous stirring under a nitrogen atmosphere fed into the top of the reaction flask. The temperature was increased to 190°–195° C. and the distillation head temperature was observed to drop from 138° C. to 104° C. over ½, at which point a slow product takeoff (40/1 reflux to takeoff) was begun. Over the next 24 hours 596 g of distillate were recovered. The distillate contained 25% starting material and 75% 2,3-difluoro-5-(trifluoromethyl)pyridine equivalent to 447 g (81% yield) based on KF.

EXAMPLE 9

A 2 liter 3-necked flask was equipped with an efficient stirrer, a 1 inch ID seven tray glass Oldershaw (sieve plate) distillation column having a vapor fraction cutter condenser and a water-jacketed receiver. The apparatus was also fitted with a thermometer, temperature controller, 250 W infrared heat lamp, and an efficient reduced pressure control device. To this apparatus was charged 1200 ml of dimethylsulfoxide (DMSO). The mixture was heated with stirring under a pressure of 150 mmHg to reflux, and ca. 35 ml of the solvent was distilled at 136 °–139° C./150 mm to dry the system. The vacuum was released, and there was added 213 g (1.4 g-mol) of cesium fluoride, which had been dried in vacuo at 250° for 24 hours and then pulverized, followed by 6 g of potassium carbonate and 199.5 g (1.0 g-mol) of 2-fluoro-3-chloro-5-(trifluoromethyl)pyridine. The pressure was again reduced to 150 mmHg, and the mixture was heated with vigorous stirring to reflux. The distillation head temperature was observed to drop to 70°/150 mm after 30 minutes. Distillation was then begun and maintained at 5:1 reflux over the next 4½ hours, during which time 163.7 g of liquid was removed, b.p. 67°–74°/150 mm; during the final 15 minutes of the reaction, the head temperature increased rapidly to 136° C. The pot temperature was steadily increased from an initial 122° C. to 140° C. over the five hours of reaction time. Gas-liquid phase chromatograph (glpc) analysis of the product showed the presence of 144.7 g (79 percent yield) of 2,3-difluoro-5-(trifluoromethyl)pyridine and 9 percent recovery of 3-chloro-2-fluoro-5-(trifluoromethyl)pyridine. The net yield of the desired product was therefore 87 percent at 91 percent conversion.

EXAMPLE 10

Preparation of 2,3-difluoro-5-(trifluoromethyl)pyridine Showing the Effect of not Drying the System on the Yield The apparatus and procedure was essentially the same as in Example 9 excepting that the CsF was not pre-dried and the system-drying step (distillation of DMSO prior to adding the other reactants) was omitted. The initial head temperature was 120° C./150 mm, and distillation of the product as it was formed was at 66°–82° C./150 mm over 5 hours. The distillate weighed 140.2 g and was found to contain 130.7 g of 2,3-difluoro-5-(trifluoromethyl)pyridine and 2.2 g of starting material (74 percent yield at 97 percent conversion).

EXAMPLE 11

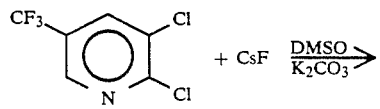 + CsF 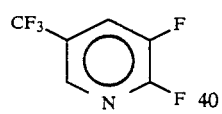 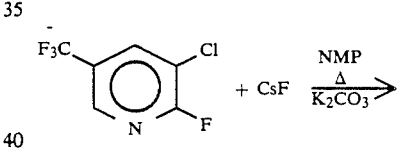

To the apparatus described in Example 1 was charged 600 ml of DMSO, and ca. 30 ml of DMSO were distilled at 136° C./150 mm to dry the system. There was then added 160 g (1.05 mole) of dry CsF, 100 g (0.46 mole) of 2,3-dichloro-5-(trifluoromethyl)pyridine and 3 g of K$_2$CO$_3$. The mixture was heated with stirring to reflux at 150 mm for 1 hour, during which time the head temperature dropped to ca. 90° C. Slow distillation was then begun, there being recovered 20.2 g of product consisting mostly of 2,3-difluoro-5-(trifluoromethyl)pyridine over 5 hours.

Distillation was interrupted at this point and the mixture was allowed to stir at 135° C. overnight. Continuation of the distillation gave an additional 63.7 g of material b.p. 58°–137°/150 mm. Analysis of the combined products by glpc showed the presence of 39.2 g of 2,3-difluoro-5-(trifluoromethyl)pyridine and 25.3 g of 3-chloro-2-fluoro-5-(trifluoromethyl)pyridine.

EXAMPLE 12

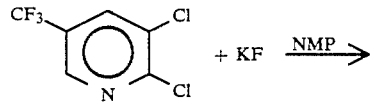 + KF $\xrightarrow{\text{NMP}}$

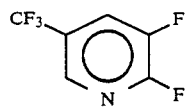

To the apparatus described in Example 1 was charged 500 ml of NMP and 32 g (0.55 mole) of dry KF. Ca. 30 ml of NMP was distilled at 106°–139° C./125 mm to dry the system and then 108 g (0.5 mole) of 2,3-dichloro-5-(trifluoromethyl)pyridine was added. The mixture was heated to 140° C. for 4½ hours. Glpc analysis of a sample showed that conversion to the intermediate, 3-chloro-2-fluoro-5-(trifluoromethyl)pyridine, was only ca. 70% complete, so an additional 28 g (0.5 mole) of dry KF was added. Conversion to the intermediate was found to be complete after an additional 1 hour, so 28 g (0.5 mole) more of dry KF was added, and the mixture was heated to reflux at 1 atmosphere pressure. The head temperature dropped over ca. ½ hour to ca. 111° C., and takeoff of ca. 10 g of product was initiated over the next ½ hour before the reaction was shut down overnight.

Resumption of distillation yielded an additional 60 g of product, b.p. 110°–180° C. over 3½ more hours before sampling disclosed the absence of further volatiles other than NMP.

Analysis of the product by glpc showed the presence of 59.1 g of 2,3-difluoro-5-(trifluoromethyl)pyridine and 8.1 g of 3-chloro-2-fluoro-5-(trifluoromethyl)pyridine (77% yield of IV at 84% conversion).

EXAMPLE 13

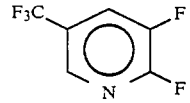

To a 2 l flask, equipped as described in Example 1, was charged one liter (1 l) of N-methyl pyrrolidinone (NMP) which was heated under a vacuum of 20 mmHg at 120° C. to dry the system. About 20 ml of NMP and water were removed. The vacuum was released and 152 g (1.0 mole) of CsF (dried in vacuo 24 hours at 140°–160° C. and then pulverized), 10 g of K$_2$CO$_3$ (anhydrous) and 200 g (1.0 mole) of 3-chloro-2-fluoro-5-(trifluoromethyl)pyridine were added. Heating was resumed with vigorous stirring under a nitrogen atmosphere fed into the top of the reaction flask. The temperature was increased to 175° C. and then was slowly lowered to 120° C. over 4 hours, at which point product takeoff (5/1 reflux to takeoff) was begun under a vacuum of 180 mmHg. Over the next 4 hours 189 g of distillate were recovered. The distillate contained 62% 2,3-difluoro-5-(trifluoromethyl)pyridine equivalent to 117 g (64% yield) based on CsF as indicated by glpc. Overall recovery of starting material was 96.7%.

We claim:
1. A process for making a product compound of the formula

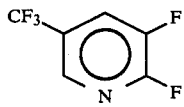

which comprises contacting, in a liquid medium, at an effective temperature of 50° C. to the boiling point of the liquid medium, and at a pressure of from 10 mmHg to 10 atmospheres, a reactant compound having the formula

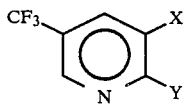

wherein X is Cl or Br and Y is Cl, Br, F, or I with an effective amount of KF, while removing the product compound by distillation essentially as it is formed, and, adding additional reactant compound as the product compound is removed.

2. Process of claim 1 wherein Y is fluorine.
3. Process of claim 1 wherein Y is chlorine.
4. Process of claim 2 wherein X is chlorine.
5. Process of claim 3 wherein X is chlorine.
6. Process of claim 1 including the additional step of carrying out the reaction in the presence of a phase-transfer catalyst selected from benzyltriethylammonium chloride, methyl trioctylammonium chloride, tetra-n-butylammonium chloride, tetra-n-butylammonium hydrogen sulfate, tetra-n-butylphosphonium chloride, cetyl trimethylammonium bromide, 18-crown-6, dicyclohexane-18-crown-6, dibenzo-18-crown-6, 15-crown-5, and tris-(3,6-dioxaheptyl)amine and optionally an acid scavenger.
7. Process of claim 1 wherein the liquid reaction medium is a polar aprotic diluent.
8. Process of claim 7 wherein the diluent is dimethylsulfoxide, sulfolane or N-methylpyrolidinone.
9. Process of claim 6 wherein the reaction temperature is from 175° C. up to the boiling point of the diluent.

* * * * *